(12) United States Patent
Capracotta et al.

(10) Patent No.: US 10,035,758 B2
(45) Date of Patent: Jul. 31, 2018

(54) METHOD OF PRODUCING AN AMINOCARBOXYLIC ACID

(71) Applicant: BASF SE, Ludwigshafen (DE)

(72) Inventors: Michael D. Capracotta, Canton, MI (US); Kenneth Zack, Wyandotte, MI (US)

(73) Assignee: BASF SE (DE)

( * ) Notice: Subject to any disclaimer, the term of this patent is extended or adjusted under 35 U.S.C. 154(b) by 0 days.

(21) Appl. No.: 15/102,652

(22) PCT Filed: Dec. 9, 2014

(86) PCT No.: PCT/US2014/069227
§ 371 (c)(1),
(2) Date: Jun. 8, 2016

(87) PCT Pub. No.: WO2015/089012
PCT Pub. Date: Jun. 18, 2015

(65) Prior Publication Data
US 2016/0311758 A1      Oct. 27, 2016

Related U.S. Application Data

(60) Provisional application No. 61/913,444, filed on Dec. 9, 2013.

(51) Int. Cl.
*C07C 227/18*      (2006.01)

(52) U.S. Cl.
CPC .................. *C07C 227/18* (2013.01)

(58) Field of Classification Search
CPC ................................................... C07C 227/18
See application file for complete search history.

(56) References Cited

U.S. PATENT DOCUMENTS

| 3,535,373 | A | 10/1970 | Jackisch |
| 4,782,183 | A | 11/1988 | Goto et al. |
| 5,817,864 | A | 10/1998 | Greindl et al. |
| 5,849,950 | A | 12/1998 | Greindl et al. |
| 7,621,281 | B2 | 11/2009 | Ikemoto et al. |
| 7,671,234 | B2 | 3/2010 | Oftring et al. |

| 2002/0046427 | A1 | 4/2002 | Nambu et al. |
| 2011/0180101 | A1 | 7/2011 | Konishi et al. |
| 2012/0097392 | A1 | 4/2012 | Reyes et al. |
| 2014/0343289 | A1* | 11/2014 | Ohnuki ................. C07C 227/42 546/245 |

FOREIGN PATENT DOCUMENTS

| CA | 1196476 A | 11/1985 |
| CA | 2834110 A1 | 11/2012 |
| DE | 19712012 A1 | 9/1998 |
| WO | WO2009/127982 A2 | 10/2009 |

OTHER PUBLICATIONS

Zaragoza Dorwald (Side Reactions in Organic Synthesis, 2005, WILEY-VCH Verlag GmbH & Co. KGaA, Weinheim, Preface. p. IX.*
Hursthouse et al, Organic Process Research & Development, Why Do Organic Compounds Crystallize Well or Badly or Ever so Slowly? Why is Crystallization Nevertheless Such a Good Purification Technique?, 2009, 13, 1231-1240.*
Stein et al (Journal of Biological Chemistry, Aromatic Sulfonic Acids as Reagents for Amino Acids: The Preparation of L-Serine, L-Alanine. L-Phenylalanine, and L-Leucine from Protein Hydrosylates, 143, pp. 121-129).*
English language abstract and machine-assisted English language translation for DE 19712012 extracted from espacenet.com database on Jul. 11, 2016, 4 pages.
International Search Report for PCT/US2014/069227, dated Feb. 25, 2015, 3 pages.

* cited by examiner

*Primary Examiner* — Paul A Zucker
(74) *Attorney, Agent, or Firm* — Drinker Biddle & Reath LLP

(57) ABSTRACT

An aminocarboxylic acid is produced from a solution that includes an aminocarboxylate and a solvent. A method of producing the aminocarboxylic acid comprises the step of combining a sulfonic acid and the solution comprising the aminocarboxylate and the solvent to produce a composition. An example of the aminocarboxylate is a salt of methylglycine diacetic acid (MGDA). An example of the sulfonic acid is methane sulfonic acid (MSA). The composition comprises the aminocarboxylic acid. The method further comprises the step of isolating the aminocarboxylic acid from the composition.

18 Claims, No Drawings

METHOD OF PRODUCING AN AMINOCARBOXYLIC ACID

CROSS REFERENCE TO RELATED APPLICATIONS

This application is the National Stage of International Patent Application No. PCT/US2014/069227, filed on Dec. 9, 2014, which claims the benefit of U.S. Provisional Patent Application Ser. No. 61/913,444, filed on Dec. 9, 2013, which is incorporated herewith by reference in its entirety.

FIELD OF THE INVENTION

The present invention generally relates to a method of producing an aminocarboxylic acid, and more specifically to a method of producing an aminocarboxylic acid from a solution comprising an aminocarboxylate and a solvent.

DESCRIPTION OF THE RELATED ART

Various methods of making aminocarboxylic acids are understood in the art. However, conventional methods of making aminocarboxylic acids suffer from one or more deficiencies. These deficiencies can include: introduction of additional/excess water, which requires subsequent removal; use of large quantities of harsh chemicals, which increases cost of manufacture and raises safety concerns; use of high temperatures, which also increases cost of manufacture and raises safety concerns; and/or byproduct generation, which results in contamination of the aminocarboxylic acid. Accordingly, there remains an opportunity to provide an improved method of making aminocarboxylic acids, which overcomes one or more of the aforementioned deficiencies.

SUMMARY OF THE INVENTION AND ADVANTAGES

Disclosed is a method of producing an aminocarboxylic acid from a solution. The solution comprises an aminocarboxylate and a solvent. The method comprises the step of combining a sulfonic acid and the solution comprising the aminocarboxylate and the solvent to produce a composition. The composition comprises the aminocarboxylic acid. The method further comprises the step of isolating the aminocarboxylic acid from the composition to remove the aminocarboxylic acid from the composition.

The method is useful for providing a variety of different aminocarboxylic acids, including partially or fully neutralized aminocarboxylic acids. The method generally avoids the introduction of excess water, eliminates the need for large quantities of harsh chemicals, allows for low temperature (e.g. room temperature) production of the aminocarboxylic acid, and/or provides aminocarboxylic acids having little to no byproduct contamination.

DETAILED DESCRIPTION OF THE INVENTION

Disclosed is a method of producing an aminocarboxylic acid from a solution. The solution comprises an aminocarboxylate and a solvent. Both the aminocarboxylate and the solvent are described further below. The method comprises the step of combining a sulfonic acid and the solution comprising the aminocarboxylate and the solvent to produce a composition. The composition comprises the aminocarboxylic acid as described below. The method further comprises the step of isolating the aminocarboxylic acid from the composition.

The aminocarboxylic acids and/or salts thereof are useful across a broad range of applications, and are not limited to any particular use. For example, they can be utilized in detergents for a variety of purposes. More specifically, they can be useful for stabilizing sodium perborate, and can sequester heavy metal ions in detergents. Furthermore, they can also be effective builders for phosphate-free dishwater detergents, such as by preventing hard water salts from forming scale on surfaces of dishes and contributing to increased detergency. The aminocarboxylic acids and/or the salts thereof are useful for various types of cleaners. For example, they can be utilized as chelating agents in dairy cleaners where temperatures exceed 80° C. They can also find uses in textile applications, where aminocarboxylic acids are particularly effective for removing hard ions from textile fabrics in the neutral and soda-alkaline pH ranges. The aminocarboxylic acids and/or the salts thereof are also useful in soap applications. More specifically, they can be added to curd soap, milled soap, and neat soap to prevent the soap from becoming rancid or discolored and to inhibit precipitation.

Aminocarboxylic acids and/or the salts thereof can also be utilized in metal plating processes. More specifically, they can be utilized as complexing agents in electroless copper plating baths during the production of printed circuit boards, etc. They can also be employed in alkaline plating baths for zinc and zinc alloys. Aminocarboxylic acids and/or the salts thereof can also be utilized in the oil and gas industry to dissolve precipitated metals. Aminocarboxylic acids and/or the salts thereof are also useful in the water softening industry to prevent lime soaps from being formed, and soften both cooling and industrial process water. This disclosure is not limited to any particular use of the aminocarboxylic acid and/or the salt thereof, and those of skill in the art appreciate additional or alternate uses of aminocarboxylic acids and/or the salts thereof.

Typically, the solvent is water. However, in alternative embodiments the solvent is non-aqueous. The non-aqueous solvent comprises polarizing solvents. Polarizing solvents are solvents that are capable of disassociating a salt. The solvent may also comprise both aqueous and non-aqueous solvents. In other words, the solvent may comprise both water and polarizing solvents. Generally, when the solution comprises both aqueous and non-aqueous solvents, the non-aqueous solvent is water miscible.

Various types of aminocarboxylates may be utilized. In various embodiments, the aminocarboxylate comprises a compound containing one or more nitrogen atoms bonded to a carbon chain that contains one or more carboxylate groups. When the aminocarboxylate comprises more than one nitrogen atom and each nitrogen atom is bonded to a carbon chain that contains a carboxylate group (i.e., aminocarboxylate also has more than one carboxylate group), the aminocarboxylate may be referred to as a polyaminocarboxylate. The carbon chain may comprise one or more carbon atoms. As understood in the art, the carboxylate group is the salt form of a carboxylic acid. In certain embodiments, the aminocarboxylates are salts of polyaminoacetates, such as ones containing from 1 to 6, 2 to 5, or 2 to 4, acetate groups. Other types of polyaminoacetates may also be used.

The aminocarboxylate can be present in the solution in various amounts. In certain embodiments, the aminocarboxylate is present in an amount of from about 1 to about 99, about 5 to about 95, about 25 to about 75, about 33 to about 66, about 40 to about 60, about 40 to about 50, or about 40, weight percent, each based on 100 parts by weight of the solution.

The solution can be of various pH ranges. In certain embodiments, the solution has a pH of from 8 to 14, 9 to 13, or 10 to 12. In other embodiments, the solution has a pH of from 2 to 8, 3 to 7, or 4 to 6.

In certain embodiments, the aminocarboxylate comprises a salt of methylglycine diacetic acid (MGDA), nitrilotriacetic acid (NTA), glycinediacetic acid (GLDA), ethylene diamine tetraacetic acid (EDTA), diethylaminetriamine pentacetic acid (DTPA), or a combination thereof. In a specific embodiment, the aminocarboxylate is a salt of MGDA. Suitable grades of MGDA are commercially available from BASF Corporation of Florham Park, N.J., under the trade name TRILON®, such as TRILON® M. Other suitable aminocarboxylates, e.g. GLDA, are commercially available from a variety of suppliers. In another embodiment, the aminocarboxylate comprises a salt of MGDA and GLDA.

Any cation can be used to form the salt of the carboxylic acid. In certain embodiments, the cation is an alkali metal, such as sodium. An example of such a salt of the carboxylic acid is trisodium MGDA ($Na_3$:MGDA). In other embodiments, the cation is potassium, calcium, magnesium, zinc, iron, copper, cobalt, manganese, or combinations thereof. In yet other embodiments, the cation is ammonium or substituted ammonium.

Different types of sulfonic acids may be utilized. In various embodiments, the sulfonic acid comprises an alkanesulfonic acid. In certain embodiments, the alkanesulfonic acid is a short chain alkanesulfonic acid, such as one containing from 1 to 8, 1 to 6, 1 to 4, or 1 to 2, carbon atoms (e.g. one having methyl, ethyl, or propyl, moieties). Other types of alkanesulfonic acids may also be used.

In specific embodiments, the alkanesulfonic acid is methanesulfonic acid (MSA; $CH_4O_3S$). Suitable grades of MSA are commercially available from BASF SE of Ludwigshafen, Del., under the trade name LUTROPUR®, such as LUTROPUR® MSA 100. MSA is a strong organic acid that is non-oxidizing, thermally stable, and capable of forming highly soluble salts. In other specific embodiments, the sulfonic acid comprises MSA, isethionic acid, ethane disulfonic acid, or combinations thereof. Isethionic acid and ethane disulfonic acid are strong organic acids that are non-oxidizing, thermally stable, and capable of forming highly soluble salts. Various combinations of the aforementioned sulfonic acids may also be utilized. For example, in one embodiment, the sulfonic acid comprises MSA and isethionic acid.

The step of combining the sulfonic acid and the solution comprising the aminocarboxylate and the solvent is not limited to any particular order of addition or method of combining. In one embodiment, the step of combining is conducted in a sequential order of first adding the sulfonic acid to the solution comprising the aminocarboxylate and the solvent to produce the composition. In an alternative embodiment, the sulfonic acid is added to the solution comprising the aminocarboxylate and the solvent to produce the composition. In yet another alternative embodiment, the sulfonic acid and the solution comprising the aminocarboxylate and the solvent are simultaneously dispensed into a vessel to produce the composition.

In certain embodiments, the composition is produced from combining components from the group consisting essentially of the sulfonic acid and the solution comprising the aminocarboxylate and the solvent. In other embodiments, the composition is produced from combining components which consist of the sulfonic acid and the solution.

The composition can be of various pH ranges. In certain embodiments, the composition has a pH of from 1 to 6, 1 to 4, or 1 to 2. The pH of the composition is generally an indicator of the amount of sulfonic acid that is combined with the solution comprising the aminocarboxylate and the solvent. In other words, the pH of the composition can be manipulated by adjusting the amount of sulfonic acid combined with the solution comprising the aminocarboxylate and the solvent.

Typically, the sulfonic acid is added in a concentrated form, i.e., the sulfonic acid has not been diluted with a solvent, such as water. For example, 100 percent active MSA, i.e., non-diluted MSA, is commercially available from the BASF SE, under the trade name LUTROPUR®. Of course, if desirable the sulfonic acid may also be diluted with a solvent such as water before the sulfonic acid is combined with the solution. It is to be appreciated that even concentrated acids marketed as 100 percent acid may still contain very small amounts of a diluting medium. When the sulfonic acid is added in a concentrated form, the amount of solvent present in the composition comprising the aminocarboxylic acid is essentially equal to the amount of solvent present in the solution comprising the aminocarboxylate. In this context, "essentially equal" is meant to account for the fact that even 100 percent active sulfonic acid may contain an amount of diluting medium (i.e., solvent) that is very small in comparison to the amount of sulfonic acid. For example, a 100 percent active sulfonic acid may have from about 0.50 to 0, about 0.10 to about 0, about 0.05 to 0, or about 0.01 to 0, percent diluting medium. In other words, when a concentrated sulfonic acid is combined with the solution comprising the aminocarboxylate and the solvent, the amount of solvent present in the composition is the amount of solvent present in the solution and a very small amount, if any, of the diluting medium introduced with the sulfonic acid.

Combining the sulfonic acid and the solution comprising the aminocarboxylate and the solvent removes (or dissociates) the cation (e.g. sodium) from the carboxylate group of the aminocarboxylate and produces the aminocarboxylic acid (e.g. MGDA). Adding one mole of sulfonic acid generally removes one mole of the cation. In other words, amount of sulfonic acid combined with the aminocarboxylate is generally proportional to the amount of the carboxylic acid groups produced (or dissociated carboxylate groups). The aminocarboxylic acid can still contain carboxylate groups so long as at least one carboxylic acid group is produced (i.e., free of the cation).

In certain embodiments, the amount of sulfonic acid combined with the solution comprising the aminocarboxylate and the solvent is sufficient to remove all of the cations from the aminocarboxylate, and as such, the aminocarboxylic acid contains only (free) carboxylic acid groups and no carboxylate groups. In other embodiments, the amount of sulfonic acid combined with the solution comprising the aminocarboxylate and the solvent produces the aminocarboxylic acid with three carboxylic acids groups and one carboxylate group, or alternatively, produces the aminocarboxylic acid with two carboxylic acid groups and two carboxylate groups. Various ratios of carboxylic acid groups and carboxylate groups can be produced depending on the type of aminocarboxylate, amount of aminocarboxylate, type of the sulfonic acid, and/or amount of the sulfonic acid.

The step of isolating should not be construed as being limited to any particular means for accomplishing the step of isolation. The step of isolating the aminocarboxylic acid from the composition may also result in the precipitation of the aminocarboxylic acid. The step of isolating the aminocarboxylic acid from the composition may include a single event or multiple events to accomplish the step of isolating the aminocarboxylic acid.

Example events include, but are not limited to, agitating the composition by mechanical force such as stirring; agitating the composition by non-mechanical means such as sonication; rapid changes in temperature; allowing the composition to sit for an extended period of time while exposed to temperatures below 18° C.; filtering; decanting; centrifugation; and/or solid phase extraction. In certain embodiments, the aminocarboxylic acid is isolated by mechanically stirring the composition to precipitate the aminocarboxylic acid and filtering the aminocarboxylic acid to isolate the aminocarboxylic acid from the composition.

Without departing from the broadest scope of the disclosure, filtering the aminocarboxylic acid may be performed by using any solid filtering technique capable of isolating the aminocarboxylic acid. Suitable filter techniques may include filter presses, filter belts, and filters with pore sizes in the range of from about 0.1 microns to about 10 microns. One of ordinary skill in the art can determine an appropriate filter via routine experimentation.

The step of isolating the aminocarboxylic acid can be conducted at various temperatures. In certain embodiments, the aminocarboxylic acid is isolated at a temperature of from about 0 to about 100, about 20 to about 80, or about 40 to about 60° C. In certain embodiments, the aminocarboxylic acid is isolated at a temperature of from about 0 to about 60, about 10 to about 40, about 20 to about 30, about 20 to about 24° C., or at about room temperature (e.g. 22° C.+/−1° C.). For example, the aminocarboxylic acid can be isolated at room temperature without applying heat or removing heat from the composition. The aforementioned temperatures generally pertain to the temperature of the composition itself, and not the surrounding/ambient environment. The temperature that the aminocarboxylic acid is isolated at may depend on the particular type or types of aminocarboxylic acid being isolated. For example, MGDA may be isolated at a temperature at about room temperate, and EDTA may be isolated at a temperature at about 80° C. Suitable temperatures for these aminocarboxylic acids can be determined via routine experimentation.

Typically, the aminocarboxylic acid produced is substantially free of byproducts, and more specifically salt byproducts. Salt byproducts are generally avoided by selection of the sulfonic acid. The sulfonic acid, e.g. MSA, forms a sulfonate with the cation that is removed from the aminocarboxylate. Sulfonates are highly soluble salts, and typically remain in the solution, even at temperatures below 20° C. The high solubility of the sulfonate at low temperature prevents the salt from precipitating during isolation of the aminocarboxylic acid. As a result, the aminocarboxylic acid is substantially free of salt byproducts. In this context, "substantially free" means that some salt byproduct may be present in an amount of from 0 to 5, 0 to 4, 0 to 3, 0 to 2, 0 to 1, 0 to 0.5, 0 to 0.1, 0 to 0.05, or 0 to 0.01, weight percent each based on 100 parts by weight of the aminocarboxylic acid.

In addition, the solubility of the aminocarboxylic acid is generally less at lower temperatures compared to the solubility of the aminocarboxylic acid at higher temperatures. Thus, the aminocarboxylic acid is generally easier to isolate at lower temperatures. As such, it is believed that utilizing temperatures at or near room temperature increases the yield of the aminocarboxylic acid.

Selecting an acid other than the sulfonic acid, such as sulfuric acid, can also be used to remove the cation from the aminocarboxylate. However, the resulting salt that is formed from the sulfuric acid is not soluble (i.e., the sulfuric acid salt precipitates) at room temperatures. Thus, if the aminocarboxylic acid is isolated at room temperature using sulfuric acid, the aminocarboxylic acid will be contaminated with the salt formed from the sulfuric acid and the cation. As such, if sulfuric acid is chosen, the step of isolation needs to be conducted at a high temperature to keep the salt in the composition. However, increasing the temperature of the composition further solubilizes the aminocarboxylic acid as described above. Thus, isolating the aminocarboxylic acid at a high temperature reduces or completely eliminates the yield of the aminocarboxylic acid.

Moreover, the selection of the sulfonic acid is further advantageous because sulfonic acids are commercially available in 100 percent concentrated form. Using a sulfonic acid in 100 percent concentrated form avoids diluting the composition with excess diluting medium, e.g. water. Diluting the composition is not desirable because dilution further solubilizes the aminocarboxylic acid. For example, selecting a strong acid such as hydrochloric acid (HCl) will also remove the cation from the aminocarboxylate. However, HCl is only commercially available at concentrations just over 40 percent. Therefore, using HCl is not desirable because it also adds water to the composition which further solubilizes the aminocarboxylic acid. Further solubilizing the aminocarboxylic acid is not desirable, because it decreases the ability to efficiently isolate the aminocarboxylic acid during the step of isolation.

In further embodiments, the method neutralizes the aminocarboxylic acid. In these embodiments, the method further comprises the step of combining a counter ion, the aminocarboxylic acid, and a solvent to neutralize the aminocarboxylic acid. Typically, the solvent is water. However, the solvent may comprise water, the polarizing solvent, or a combination thereof.

The counter ion, the aminocarboxylic acid, and solvent can be combined simultaneously or in any sequence. In other words, this disclosure is not limited to any particular order in which the counter ion, the aminocarboxylic acid, and solvent are combined. For example, the aminocarboxylic acid can be combined with water and then the counter ion is combined. In another example, water can be combined with the counter ion and then combined with the aminocarboxylic acid. In yet another example, the aminocarboxylic acid is combined with the counter ion and then water is combined.

Any counter ion suitable for forming a salt with the carboxylic acid may be used. In certain embodiments, the counter ion is ammonium, substituted ammonium, potassium, calcium, magnesium, zinc, iron, copper, cobalt, manganese, and/or combinations thereof. For example, in one embodiment where corrosion is a concern, ammonium and/or potassium is selected as the counter ion so that the aminocarboxylate does not contribute to a potential corrosion issue. In another embodiment where the aminocarboxylate will be used in a micronutrient product for crops or ornamental plants or food applications, calcium, iron, magnesium, copper, cobalt, or manganese is selected as the counter ion.

The aminocarboxylic acid may be a partially or fully neutralized aminocarboxylic acid. A partially or fully neutralized aminocarboxylic acid is the aminocarboxylic acid, which has been neutralized with the counter ion. An aminocarboxylic acid undergoes neutralization when the counter ion combines with at least one of the carboxylic acid groups of the aminocarboxylic acid. The counter ion, once combined with the aminocarboxylic acid, forms a salt with a carboxylic acid group to produce a carboxylate group. The fully neutralized aminocarboxylic acid is the aminocarboxylic acid where all of the carboxylic acid groups have combined with the counter ion. In other words, the fully neutralized aminocarboxylic acid has all carboxylate groups and no (free) carboxylic acid groups. The partially neutralized aminocarboxylic acid is the aminocarboxylic acid which has at least one carboxylic acid group and at least one carboxylate group. For example, a partially neutralized aminocarboxylic acid may have one carboxylic acid group and two carboxylic acid groups which have been neutralized with the counter ion. Various degrees of neutralization can be achieved depending on the types and/or amounts of components utilized.

EXAMPLES

A solution comprising water and trisodium MGDA (e.g. TRILON® M) having a pH of 10 is combined with 100 percent active MSA (e.g. LUTROPUR® MSA 100) in a vessel to form the composition comprising the aminocarboxylic acid and water. The temperature of the composition is at or near room temperature (e.g. approximately 22° C.+/−1° C.). The amount of 100 percent active MSA utilized is sufficient to produce a composition having a pH of about 2 and remove (disassociate) all of the sodium ions from trisodium MGDA. The composition is mechanically stirred to precipitate the aminocarboxylic acid. The aminocarboxylic acid is further isolated from the composition by filtering the composition to remove the aminocarboxylic acid from the composition. Filtration is accomplished using standard filtration equipment. The isolated aminocarboxylic acid is substantially free of the MSA/sodium salt. Said another way, the salt resulting from the association of the MSA and the sodium ion removed from the trisodium MGDA remains in the water after the aminocarboxylic acid is filtered. The aminocarboxylic acid is then combined with a magnesium counter ion and water. The amount of magnesium counter ion combined with the aminocarboxylic acid is sufficient to fully neutralize all of the carboxylic acid groups of the aminocarboxylic acid. In another example, the amount of magnesium counter ion combined with the aminocarboxylic acid is sufficient to neutralize 80 percent of the carboxylic acid groups and produce a partially neutralized aminocarboxylic acid.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

Further, any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The invention has been described in an illustrative manner, and it is to be understood that the terminology which has been used is intended to be in the nature of words of description rather than of limitation. Many modifications and variations of the present invention are possible in light of the above teachings. The invention may be practiced otherwise than as specifically described. The subject matter of all combinations of independent and dependent claims, both singularly and multiply dependent, is herein expressly contemplated.

What is claimed is:

1. A method of producing an aminocarboxylic acid comprising the steps of:
  combining a sulfonic acid and a solution comprising an aminocarboxylate and a solvent to produce a composition comprising the aminocarboxylic acid; and isolating the aminocarboxylic acid from the composition and wherein the step of isolating the aminocarboxylic acid is conducted at a temperature of from 0° C. to 100° C., wherein the step of isolating the aminocarboxylic acid comprises sonicating the composition and filtering the composition to remove the aminocarboxylic acid from the solution.

2. The method as set forth in claim 1 wherein the solvent comprises water, a polarizing solvent, or a combination thereof.

3. The method as set forth in claim 1 wherein the aminocarboxylic acid is free of salt byproducts after the step of isolating the aminocarboxylic acid.

4. The method as set forth in claim 3 further comprising combining a counter ion, the aminocarboxylic acid, and water to neutralize the aminocarboxylic acid.

5. The method as set forth in claim 4 wherein the counter ion comprises ammonium, potassium, calcium, magnesium, zinc, iron, copper, cobalt, manganese, or combinations thereof.

6. The method as set forth in claim 1 wherein the solution comprising the aminocarboxylate is aqueous and has a pH of from 8 to 14.

7. The method as set forth in claim 3 wherein the solution comprising the aminocarboxylate is aqueous and has a pH of from 10 to 12.

8. The method as set forth in claim 1 wherein the composition comprising the aminocarboxylic acid has a pH of from 1 to 6.

9. The method as set forth in claim 1 wherein the aminocarboxylate comprises a salt of methylglycine diacetic acid (MGDA).

10. The method as set forth in claim 3 wherein the aminocarboxylate comprises a salt of an acid selected from the group of methylglycine diacetic acid (MGDA), nitrilotriacetic acid (NTA), glycinediacetic acid (GLDA), ethylene diamine tetraacetic acid (EDTA), diethylaminetriamine pentacetic acid (DTPA), and combinations thereof.

11. The method as set forth in claim 9 wherein the sulfonic acid comprises methane sulfonic acid (MSA).

12. The method as set forth in claim 1 wherein the sulfonic acid comprises methane sulfonic acid (MSA), isethionic acid, ethane disulfonic acid, or combinations thereof.

13. The method as set forth in claim 1 wherein the amount of solvent present in the composition comprising the aminocarboxylic acid is equal to the amount of solvent present in the solution comprising the aminocarboxylate.

14. A method of producing an aminocarboxylic acid comprising the steps of:
combining a sulfonic acid and a solution comprising an aminocarboxylate and water to produce a composition having a pH of from 1 to 4 and comprising the aminocarboxylic acid; and
isolating the aminocarboxylic acid from the composition at a temperature of from 10° C. to 40° C.,
wherein the isolated aminocarboxylic acid is free of salt byproducts, wherein the aminocarboxylate comprises a salt of an acid selected from the group of methylglycine diacetic acid (MGDA), nitrilotriacetic acid (NTA), glycinediacetic acid (GLDA), ethylene diamine tetraacetic acid (EDTA), diethylaminetriamine pentacetic acid (DTPA), and combinations thereof.

15. The method as set forth in claim 14 further comprising combining a counter ion, the aminocarboxylic acid, and water to neutralize the aminocarboxylic acid.

16. The method as set forth in claim 14 wherein the step of isolating comprises the steps of agitating the composition and filtering the composition to remove the aminocarboxylic acid from the composition.

17. The method as set forth in claim 14 wherein:
i) the aminocarboxylate comprises a salt of methylglycine diacetic acid (MGDA);
ii) the sulfonic acid comprises methane sulfonic acid (MSA); or
iii) both i) and ii).

18. The method as set forth in claim 1 wherein the sulfonic acid comprises an alkanesulfonic acid.

* * * * *